United States Patent [19]

Shim

[11] Patent Number: 4,745,226

[45] Date of Patent: May 17, 1988

[54] REACTION OF SULFUR WITH POLYCHLORINATED POLYPHENYLS

[75] Inventor: Kyung S. Shim, Irvington, N.Y.

[73] Assignee: Stauffer Chemical Company, Westport, Conn.

[21] Appl. No.: 909,812

[22] Filed: Sep. 22, 1986

[51] Int. Cl.$^4$ .......................................... C07C 149/00

[52] U.S. Cl. .......................................... 568/25; 568/24

[58] Field of Search .............................. 568/24, 25, 56

[56] References Cited

U.S. PATENT DOCUMENTS 2,402,685 6/1946 Signaigo .............................. 568/25

FOREIGN PATENT DOCUMENTS 1222768 2/1971 United Kingdom ................. 568/25

OTHER PUBLICATIONS

E. Reid, Organic Chemistry of Bivalent Sulfur, vol. III, p. 365, QD 412.S1R4 (1960), Chem. Publishing Co., N.Y.

S. Oae et al, Chem. Abstracts, vol. 82, No. 155718g (1975), Converting Polychlorinated Biphenyls to Innocuous Substances.

H. Miyake et al, Chem. Abstracts, vol. 84, No. 107840k (1976), Activated Carbon from an Aromatic Chloride.

*Primary Examiner*—Mary E. Ceperley

*Attorney, Agent, or Firm*—Richard P. Fennelly

[57] ABSTRACT

Polychlorinated polyphenyl materials are reacted with sulfur in the presence of an effective amount of a sulfur chloride compound to result in a product having a lowered residue of chlorinated polyphenyl as compared to a reaction practiced without the use of the compound.

9 Claims, No Drawings

REACTION OF SULFUR WITH POLYCHLORINATED POLYPHENYLS

BACKGROUND OF THE PRESENT INVENTION

1. Field of the Present Invention

The present invention is an improved reaction of sulfur with a polychlorinated polyphenyl material to convert the polyphenyl material to a more innocuous substance.

2. Description of the Prior Art

Japanese Kokai No. 74/127,954 indicates that polychlorinated biphenyls can be converted to innocuous substances by heating them with sulfur. The resulting products are presumed to be biphenylene polysulfides.

SUMMARY OF THE PRESENT INVENTION

It has now been found that the use of a sulfur chloride compound, e.g. sulfur monochloride, in such a reaction, results in a promotion of the reaction of sulfur with the polychlorinated polyphenyl material so that the product which is formed thereby has a lower residual amount of unreacted chlorinated polyphenyl residue therein.

DETAILED DESCRIPTION OF THE PRESENT INVENTION

The present invention is applicable to the reaction of sulfur, preferably in excess stoichiometric amount, with a polychlorinated polyphenyl material at elevated temperature (e.g. from about 300° C. to about 400° C.) for a sufficient amount of time to result in the formation of a solid product therefrom. The solid product has not been completely characterized but is greatly reduced in regard to its residual amounts of chlorinated polyphenyl reagent which originally was present in the reaction vessel.

In accordance with the present invention, it is contemplated that an effective amount (e.g. from about 0.1% to about 50% by weight of the polychlorinated polyphenyl material, preferably 0.1–10%, by weight) of sulfur chloride compound is present when the sulfur and the polyphenyl material are reacted. A representative sulfur chloride compound which can be used as a promoter in the present invention is sulfur monochloride ($S_2Cl_2$). As shown in the Examples which follow, the use of the sulfur chloride compound in the aforementioned type of reaction results in a lowered amound of chlorinated polyphenyl residue in the solid product formed by the reaction of sulfur and the polychlorinated polyphenyl material under the conditions described herein.

The foregoing promoted reaction is useful with both polychlorinated biphenyl and polychlorinated terphenyl materials as is demonstrated in the Examples.

The present invention is further illustrated in the Examples which follow which illustrate, in Examples 2–4, certain embodiments of the present invention. Comparative Example 1 is presented to illustrate the inferior results that were obtained when a non-promoted reaction of sulfur and polychlorinated biphenyl was conducted.

COMPARATIVE EXAMPLE 1

This Example shows the results obtained when a non-promoted reaction of sulfur and polychlorinated biphenyl (AROCLOR brand) was conducted without promotor as generally suggested in Japanese Kokai No. 74/127,954.

Sulfur (19.2 gm.) and the polychlorinated biphenyl composition (26 gm.) were reacted at 300° C.–320° C. for about 3 hours while trapping evolved sulfur monochloride ($S_2Cl_2$) in sodium hydroxide. The resulting solid product was washed with $CS_2$ several times and left overnight to dry. Extractable soluble sulfur was stripped on a rotaty evaporator.

Gas chromatographic (GC)/mass spectrophotometer (MS) analysis of the solid product showed about 160 ppm of chlorinated biphenyl residue.

EXAMPLE 2

Into a 1-liter resin kettle fitted with a thermometer, dropping funnel and mechanical stirrer was placed 500 gm. of sulfur which was heated to 330° C. While agitation was supplied, 100 gm. of polychlorinated biphenyl composition containing 5 drops of $S_2Cl_2$ (about 0.25–0.3 gm.) as a promoter was added dropwise over a period of about 2 hours. The reaction temperature was 300° C.–370° C., mostly about 340° C. The reddish-brown product was washed with $CS_2$ and dried. It was then ground, washed several more times with $CS_2$, and dried overnight.

GC/MS analysis failed to detect any chlorinated biphenyl residue. The limit of detection was 10 ppm.

EXAMPLE 3

The procedure of Example 2 was repeated using 90 gm. of polychlorinated biphenyl with a slightly more fluid version (less viscous) of the polychlorinated biphenyl product. The reaction temperature was 315° C–375° C., mostly 350° C.

GC/MS analysis again detected no chlorinated biphenyl residue with a limit of detection of 10 ppm.

EXAMPLE 4

Example 2 was repeated using a polychlorinated terphenyl material rather than the biphenyl material treated in that Example. The terphenyl material was heated prior to use and mixed with the sulfur prior to placement in a 1-liter resin kettle fitted with thermometer and heater. The reaction was performed at 320° C. and continued for about 1.5 hours.

GC/MS analysis of the product showed just under 30 ppm chlorinated terphenyl residue.

The foregoing Examples are presented to merely illustrate certain preferred embodiments of the present invention. The scope of protection which is sought is set forth in the claims which follow.

I claim:

1. In a process of reacting sulfur with a polychlorinated polyphenyl material to convert the polyphenyl material to a more innocuous substance, the improvement which comprises the additional use of an effective amount of a sulfur chloride to promote the reaction and yield a lowered amount of unreacted chlorinated polyphenyl residue in the product formed.

2. A process as claimed in claim 1 wherein the sulfur chloride is sulfur monochloride.

3. A process as claimed in claim 1 wherein the polychlorinated polyphenyl material is polychlorinated biphenyl.

4. A process as claimed in claim 1 wherein the polychlorinated polyphenyl material is polychlorinated terphenyl.

5. A process as claimed in claim 3 where the sulfur chloride is sulfur monochloride.

6. A process as claimed in claim 4 where the sulfur chloride is sulfur monochloride.

7. A process as claimed in claim 1 wherein the effective amount ranges from about 0.1% to about 50% by weight of the polychlorinated polyphenyl material.

8. A process as claimed in claim 5 wherein the effective amount ranges from about 0.1% to about 50% by weight of the polychlorinated polyphenyl material.

9. A process as claimed in claim 6 wherein the effective amount ranges from about 0.1% to about 50% by weight of the polychlorinated polyphenyl material.

* * * * *